United States Patent [19]

Millet

[11] 4,181,223

[45] Jan. 1, 1980

[54] SELF-PACKAGED MEDICAL DEVICE WITH FRANGIBLE SEAL

[75] Inventor: Marcus J. Millet, New York, N.Y.

[73] Assignee: Johnson & Johnson, New Brunswick, N.J.

[21] Appl. No.: 909,335

[22] Filed: May 25, 1978

[51] Int. Cl.² ............... B65D 85/00; B65D 17/16; A61M 5/32

[52] U.S. Cl. ............... 206/365; 215/12 R; 215/233; 220/265; 220/455

[58] Field of Search ............... 206/365, 303, 364; 215/12 R, 233, 251, 249; 220/265, 455

[56] References Cited

U.S. PATENT DOCUMENTS

| | | | |
|---|---|---|---|
| 1,664,635 | 4/1928 | Magill | 215/233 |
| 2,127,548 | 8/1938 | Boyles et al. | 215/233 |
| 2,525,358 | 10/1950 | Jenett | 206/303 |
| 2,929,525 | 3/1960 | Glover et al. | 215/12 R |
| 3,107,785 | 10/1963 | Roehr | 206/365 |

*Primary Examiner*—William T. Dixson, Jr.

[57] ABSTRACT

A self-packaged medical device has a hollow body and an operative element inside for controlling the dispensing of fluids from the device. A handle, partly inside and partly outside of the body is connected to the operative element and is provided with a frangible seal at the point where the handle passes through a hole in the wall of the body. This seal allows maintenance of cleanliness of the interior of the body during storage, but does not interfere with the use of the handle to operate the element within the body once the seal is broken. The seal is formed by a continuous, frangible film adhering to the body and the handle, and is broken by motion of the handle, whereupon the device is ready for use. A hydrodermic syringe is desirably self-packaged in this fashion.

A method of making a self-packaged hypodermic syringe includes assembling a piston, with a piston rod connected to it, into a bore of a tubular barrel so that the rod extends out of the barrel. A clearance space is left between the rod and the inside wall of the barrel. This assembly is dipped, piston rod extension facing downward, into a bath of curable liquid plastic to a sufficient depth to cause a column of liquid plastic to rise into the clearance space in the barrel. Following withdrawal of the assembly from the bath, the liquid plastic is cured to a solid form, thereby providing a seal for the self-packaged syringe.

13 Claims, 5 Drawing Figures

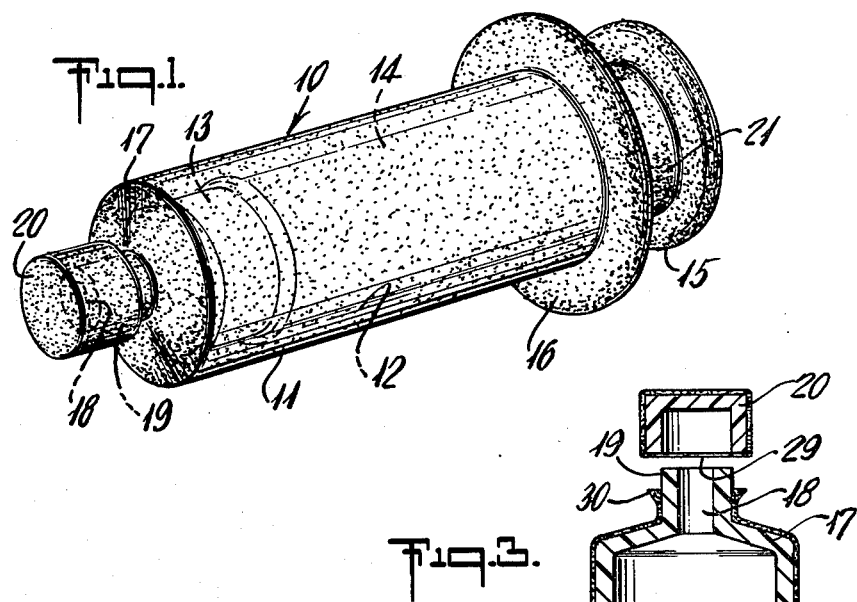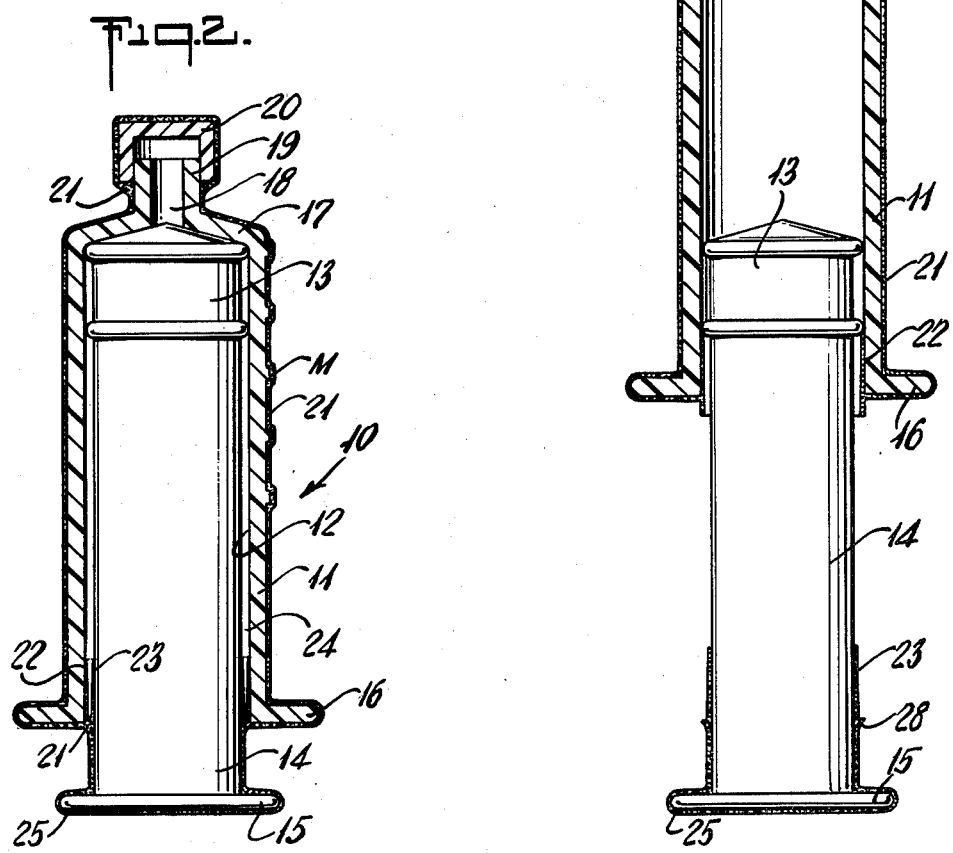

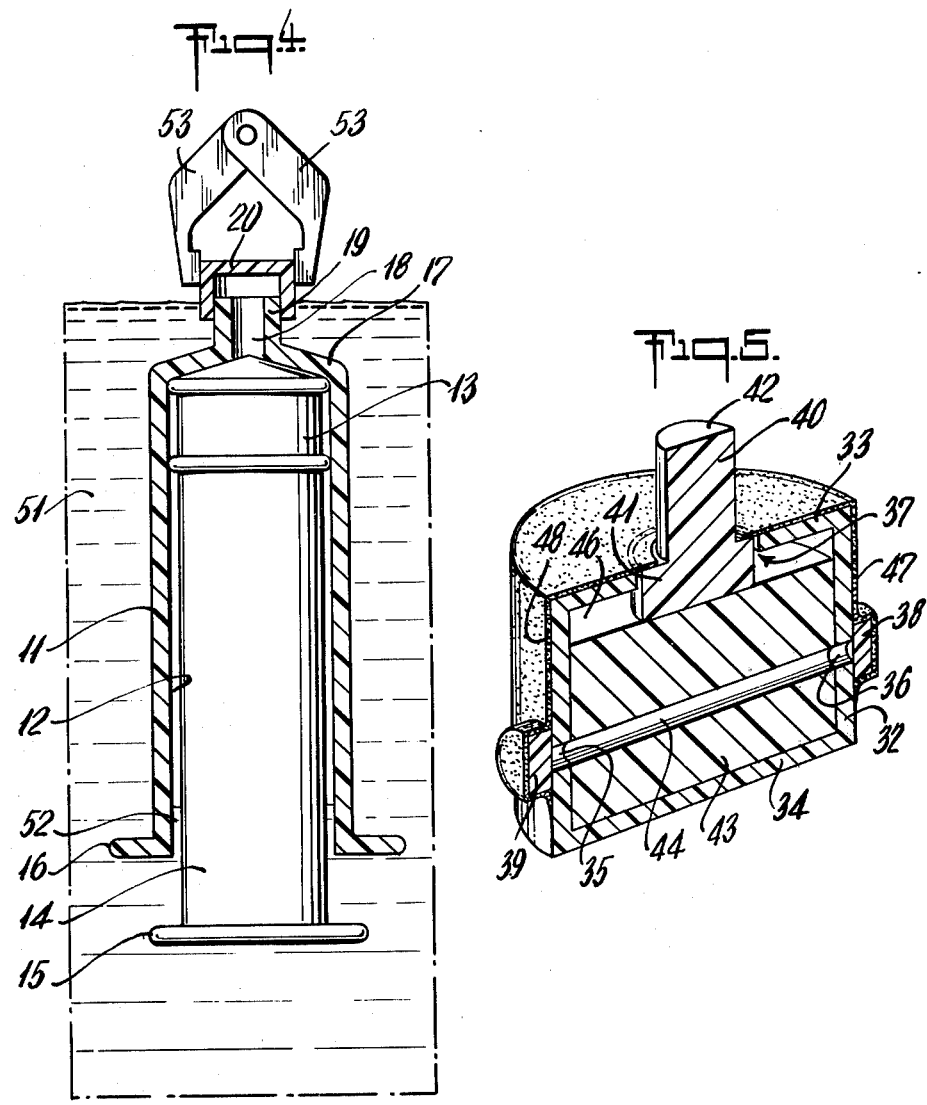

SELF-PACKAGED MEDICAL DEVICE WITH FRANGIBLE SEAL

This invention relates to medical devices which are provided in a sterile condition, and more particularly, to devices in which the exterior of the device itself forms part of a barrier to protect the interior of the device from microbial contamination during storage.

Devices provided in a pre-sterilized condition are commonly protected during storage and handling by some form of packaging which meets certain requirements. First, the packaging should effectively protect those elements of the device which will contact the patient, or which will contact fluids to be administered, from contamination by microorganisms. Second, the packaging should provide an indication to the user if it has been opened; a package which does this is called "tamper-evident" by those skilled in the art. Third, the user's access to the device should not be impeded by the need to remove and discard packaging materials. Fourth, the packaging should not impair the operation of the device during use. Fifth, the total cost of the device as packaged should preferably be as low as possible. Finally, the packaging should provide adequate mechanical protection for the device.

In the prior art, the most common method of meeting these requirements has been to enclose the entire device in a container of some sort. Such containers are available in many forms, including envelopes, vials such as shown in U.S. Pat. No. 585,007 and plastic tubes. Many methods of providing the tamper-evident feature have been employed, including frangible films as shown in U.S. Pat. No. 3,968,876.

All of these container systems provide effective protection for the entire device, but they all impede the user's access to the device and add to the cost of the device as packaged. Where the device to be protected is a fluid-handling device with a hollow body for holding the fluid, it is often unnecessary to protect the outside of the body from contamination by microorganisms; only the fluid contact surfaces within the body need be protected. For example, a bottle for intravenous infusion fluids is satisfactorily protected by merely capping the openings with the caps secured to the body of the bottle in a tamper-evident fashion. This is known as "self-packaging" to those skilled in the art, becuase the body of the device itself forms part of the protective barrier around the interior fluid contact elements of the device.

Self-packaging is useful and effective in many cases because it is generally low in cost and does not seriously impede access to the device by the user. However, it has been limited in several important respects until now. A significant difficulty arises when there is a means for controlling fluid flow positioned within the hollow body of the device, linked to a control handle which extends to the outside of the hollow body. The control handle must extend through a hole in the wall of the hollow body. Until now, there has been no truly satisfactory way of sealing this hole during storage. The most familiar example of such a device is the hypodermic syringe which has a hollow barrel defining a bore, a piston within the bore and a piston rod extending out through the open end of the bore. The open end of the bore forms a hole in the barrel which will allow entry of microorganisms unless it is completely sealed. In U.S. Pat. No. 3,828,775, a cap is shown which covers the entire exposed surface of the piston-rod, and which is secured to the barrel of the syringe by a frangible element. While such a cap effectively seals the open end of the bore during storage, it must be removed and discarded by the user, and it thus impedes his access to the device. Also, such a cap adds to the cost of the device. In U.S. Pat. No. 3,828,775, an alternative structure is recited at Column 3, lines 12–27, wherein the cap is formed by dip-coating the exposed end of the piston rod and the adjacent section of the barrel in a bath of liquid plastic material which does not adhere to the piston rod. As recited, this cap must be removed by use of a "rip-strip" technique before the syringe is used, and access to the device is again impeded. A slidable seal between the piston rod and the interior bore at its open end has been used to close the hole, but such a seal must be a tight fit to the piston rod to effectively preserve the sterility of the interior of the barrel. A slidable seal which is so tightly fit causes a substantial frictional drag on the piston rod which impairs the feel of the syringe during use. Such a seal is difficult to produce in quantity with the requisite reliability, and it requires an additional element for tamper-evidence.

Another limitation on the use of self-packaging has been felt when the body of the device is provided with markings on the outside; there has been no economical way to protect these markings from abrasion during shipment of the device. Although it has long been known that a transparent coating can be applied over the markings, the application of the coating has generally been a separate step in addition to providing a seal for the inside portions of the device. This, of course, adds expense to the manufacture of the device. Thus, it is evident that there is room for further improvements in this field.

SUMMARY OF THE INVENTION

The self-packaging medical device for dispensing liquids has a hollow body for receiving the liquid. An operative element, within the hollow body, is adapted to control the flow of liquid out of the body. Means extends from the operative element outwardly through an opening in the body for operating the element and thereby controlling the flow of the liquid. A continuous, frangible film extends from the body to the extending means and adheres to both body and extending means. The film seals the opening in the space between the body and the extending means to protect the opening from entry of contaminating media; the film is readily fractured upon operation of the extending means relative to the body whereupon the device may be used to dispense liquid.

In the preferred embodiment of this aspect of the invention, the device is a hypodermic syringe with a hollow, tubular barrel defining an interior bore which is open to the outside of the proximal end of the barrel. A distal end wall of the barrel closes the distal end of the interior bore and has a fluid flow passage therethrough. A piston is within the bore in slidable sealing engagement with the inside walls of the barrel, and a piston rod, connected to the piston, extends outwardly through the opening in the bore and outside of the barrel. A cap is releasably mounted over the fluid flow passage, the cap being removable by the user prior to using the syringe. Frangible film, such as polyvinyl chloride plastisol, extends between the barrel and the piston rod to seal the space therebetween and protect it from entry of microorganisms. An extension of the frangible film seals the cap to the barrel. The film is readily fractured, both by movement of the piston rod and removal of the cap, whereupon the syringe, in a clean condition, is ready for use.

In another embodiment of this aspect of the invention, the device is a stopcock. Its hollow body includes two flow passages for fluid to pass in and out of the body. A rotatable plug inside the body has a bore therethrough which, when aligned with and between the flow passages, allows fluid to pass through; when the bore is misaligned with the flow passages, the plug acts as a seal to prevent fluids from passing through. A handle, connected to the plug, extends out of a hole in the body and allows the user to rotate the plug inside. A frangible film extends between the handle and the body, adhering to both, and seals the hole from the entry of contaminating media. Upon rotation of the handle, the film readily fractures to thereby allow free movement of the handle and the plug and thus use of the stopcock.

Another aspect of the present invention is a method of making a self-packaged hypodermic syringe. A piston having a piston rod connected thereto is assembled into a bore of a tubular barrel so that the piston rod extends out of the barrel. A clearance space is provided between the piston rod and the inside wall of the barrel. This assembly is dipped, with the end including the extending piston rod facing downward, into a bath of curable liquid plastic material which adheres to the piston rod and barrel when cured. The dipping is to a depth sufficient to cause a column of liquid plastic to rise into the clearance space in the barrel. Following withdrawal of the assembly from the bath, the liquid plastic is cured to a solid form.

In accordance with the principles of this invention, the improved self-packaged device advantageously fulfills the requirements as set forth earlier relating to the storage and use of medical devices available in a presterilized condition. The structure of the self-packaged device of the present invention allows the device to be sealed from contamination during storage, and then to be unsealed for use by the normal movement of the parts which would have to be moved for preparation of the device even if there were no seal. Accordingly, the structural arrangement of the frangible film onto the movable parts for proper sealing of the inside of the device is notably different from other devices heretofore known in the art. An ensuing advantage of the present invention is that no cap or outside film has to be discarded in order to break the seal and make the device operable. This, of course, provides the user with quicker access to the device itself. Other advantages, as well, will become more apparent when the improved self-packaged device is described in detail.

BRIEF DESCRIPTION OF THE DRAWINGS

FIG. 1 is a perspective view of the preferred embodiment of a syringe with the frangible seal thereon;

FIG. 2 is a cross-sectional view of a syringe with the film seal after manufacture and before use of the syringe taken along line 2—2 of FIG. 1;

FIG. 3 is a sectional view of the same syringe as shown in FIG. 1, along the same plane, but depicting the syringe during use;

FIG. 4 is a sectional view of the same syringe as shown in FIG. 1, along the same plane, but depicting the syringe during the preferred dipping operation in manufacture; and FIG. 5 is a perspective cutaway view of a stopcock incorporating another embodiment of the frangible film seal.

DETAILED DESCRIPTION

While this invention is satisfied by embodiments in many different forms there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be pointed out in the appended claims.

Although the frangible film seal of this invention is applicable to a variety of self-packaged medical devices, especially those having a hollow body, an operative element within the hollow body and a handle extending from the operative element outwardly through an open end in the body, it has been found to be particularly useful for syringes and stopcocks, so its construction will be described with reference to syringes and stopcocks.

In the art of making hypodermic syringes, it is generally understood that the term "proximal" refers to the end of the syringe which is nearest to the operator during use, while the term "distal" refers to the end of the syringe which is remote from the operator and pointed toward and patient. These terms will be used to indicate the respective directions in this specification.

Referring now to FIGS. 1 and 2, syringe 10 has a conventional hollow body or barrel 11 which defines an interior bore 12. A piston 13 is positioned within bore 12 in slidable sealing engagement with the walls of the bore, and a piston rod 14 is affixed to the piston end and extends outwardly through the bore to an end outside of the barrel. Piston rod 14 is preferably provided with a button 15 and barrel 11 is provided with a flange 16 at its proximal end to facilitate gripping the syringe during use. A distal end wall 17 integral with the barrel closes the distal end of bore 12, and a fluid flow passage 18 extends through distal wall 17. Preferably a projection 19 is provided on the outside of distal wall 17 where the flow passage extends through distal wall 17 for attaching needles to the syringe. A cap 20 is releasably mounted to the outside of barrel 11, as to projection 19, and overlies the opening of flow passage 18 on the outside surface of the barrel. All of the structure related above is conventional and well-known to those skilled in the art.

The new structure for self-packing includes frangible film 21. As seen in FIGS. 1 and 2, film 21 extends from barrel 11 to piston rod 14 around the entire circumference of bore 12 to seal the bore between barrel 11 and piston rod 14 in bridging fashion. In the position shown in FIGS. 1 and 2, which is after manufacture but before use, the film completely seals bore 12 against entry of microorganisms. Adhesion of the film to barrel 11 and piston rod 12 can be achieved by means such as adhesive bonding, mechanical fastening or the like, but the preferred method is to use a dipping process as described below; thus, the adhesion of the film to the barrel and the piston rod is readily fractured when the piston rod is moved.

Piston rod 14 is preferably made with dimensions transverse to its longitudinal axis smaller than the corresponding dimensions of bore 12 to provide a clearance 24 between piston rod 14 and the walls of bore 12. Such a clearance allows relatively free motion of the piston rod and piston once film 21 has been broken.

As seen in FIGS. 1 and 2, a mass of material 22 integral with film 21 extends distally into the bore of the barrel and adheres to the walls of the bore. Mass of material 22 effectively constricts the diameter of the bore and acts as a stop for the piston as described below. A similar mass 23 is shown adhering to piston rod 14 within the bore. This mass is not functional, but is merely an artifact of the dipping process described below. Similarly, a coating 25 integral with film 21 adheres to the button 15 of piston rod 14 as an artifact of the dipping process. It is not functional, but it does not impede the use of the device in any way.

An extension of film 21 overlies and adheres to the outside of the parrel and covers the markings M on the outside of the barrel. The relative thickness of markings M has been exaggerated for clarity of illustration. This extension of the film protects the markings from abrasion during handling after manufacture. If the extension is to be provided, then the film material should be transparent. The normal use of the markings is to allow the operator to control the volume of fluid contained in the syringe by aligning the piston with the desired marking. If this use is desired, the barrel 11 should, and preferably is, also made from transparent material.

A further extension of film 21 reaches from the outside surface of barrel 11 to cap 20 and adheres to the cap and the barrel so that it will be broken by removal of the cap. If this extension of the film is continuous around the entire perimeter of the cap, the extension will completely seal flow passage 18 against the entry of microorganisms without relying on the fit of cap 20 to projection 19.

FIG. 3 shows the same syringe as shown in FIG. 2, during its use. Note that piston rod 14 has been pulled back by the operator, causing film 21 to break into a portion 27 adhering to barrel 11 and a portion 28 adhering to piston rod 14. If the film is made of a material with sufficient elongation to fracture, portions 27 and 28 will be sufficiently stretched to give a visual indication of breakage of film 21 and thus warn any subsequent user that the seal has been broken even if piston rod 14 is returned to its original position. It is apparent that broken portions 27 and 28 will touch each other if the piston rod is again advanced distally to the position shown in FIG. 2. To avoid interference with the action of the piston rod as it nears the distal end of its stroke, it is desirable that the film be made of a flexible material so that broken portions 27 and 28 will crumple without appreciable resistance when they touch each other.

Again in FIG. 3, note that cap 20 has been removed and the extension of film 21 near the cap has been broken. As with film 21, broken portions 29 and 30 of the film extension give warning that the sterility of the syringe has been breached.

Since it is a normal practice to remove cap 20 and withdraw piston 13 and piston rod 14 to the proximal end of their stroke before using a syringe, however packaged, it is apparent that a syringe which has been self-packaged in the manner shown in FIGS. 1, 2 and 3 requires no motions on the part of the user, which the user would not make in any case, and thus does not impede access to the syringe by the user. Because cap 20 is normally retained by the user for closing passage 18 during use of the syringe, no packaging materials need be discarded by the user.

The dipping process can be best understood with reference to FIG. 4, which shows the syringe being coated with film in a dipping process. At the stage shown in FIG. 4, barrel 11, piston 13, piston rod 14 and cap 20 have been assembled and the assembly is being dipped, proximal end down, into a bath of curable liquid plastic material 51 which will adhere to piston rod 14, barrel 11 and cap 20 after curing. Because piston 13 is in sealing engagement with the walls of bore 12, air cannot escape from the barrel through flow passage 18. Thus, the air trapped between the proximal end of the barrel and the piston is compressed by a rising column 52 of the liquid plastic in the clearance between the piston rod 14 and the walls of bore 12. When the assembly has been dipped to a sufficient depth, the air pressure between rising column 52 and piston 13 will cause the rise of column 52 to be stopped where the fluid head of the liquid plastic equals the air pressure. During the dipping process, the assembly may be held by grips 53 clamped to the distal end of cap 20.

After the dipping step shown in FIG. 4, the assembly is then withdrawn from the bath and any excess material is allowed to drain off. The air trapped within the barrel expands until it is again at atmospheric pressure, thus returning to its original volume, and causing the liquid plastic which entered the proximal end to be discharged until the liquid plastic assumes the shape shown in FIG. 1 as film 21. Masses 22 and 23 as seen in FIG. 2 remain where column 52 of liquid plastic contacted the wall of bore 12 and piston rod 14, respectively. The surface tension of the liquid plastic causes it to bridge clearance 24 and form film 21. Depending on the speed of cure of the particular liquid plastic being employed, the liquid plastic is cured either after the draining of the excess material or simultaneously with the draining.

If the liquid plastic is of a type which requires heating to cure it to a solid, it is desirable to preheat the assembly to at least the planned cure temperature before dipping. If this step is omitted, the air trapped within the barrel may expand to more than the volume which it had before dipping and blow out film 21 while it is being cured.

Note that mass 22 was formed simultaneously with film 21, and was not present at the assembly stage of manufacture. Thus, it could not cause difficulty in inserting piston 13 into bore 12. With reference to FIG. 3, the function of mass 22 becomes apparent. Since piston 13 is closely fit to bore 12, its travel in the proximal direction is stopped by mass 22, and it cannot be accidentally dislodged from barrel 11.

The syringe may be made of conventional materials, the most common choices being polypropylene or polyethylene for the barrel and piston rod and a filled natural or silicone rubber for the piston. The film can be made of any material which can be formed, substantially without the formation of pinholes, into a film thin enough to be readily frangible. If the dipping process described above is to be used to form the film and its extensions, then a material which may be applied as a liquid and later cured to a solid is preferably employed. If the film is to cover a graduation marking on the barrel, the film material should be transparent in its cured state. A material which possesses all of these properties is a polyvinyl chloride plastisol which is a dispersion of particles of polyvinyl chloride in dioctyl phthalate. Other curable liquid plastics may be used, including the epoxies and the polyurethanes. In the best mode of the invention known to the applicant, the piston is a silicone rubber, the barrel and piston rod are polypropylene, and the film is a cured polyvinyl chloride plastisol. To promote adhesion of the film to the barrel and piston rod, the barrel and piston rod are preferably flame-treated prior to assembly.

Of course, not all of the extensions of film 21 shown in FIG. 2 are required for successful application of the invention. If other means of closing fluid passage 18 are employed, cap 20 and the extension of film may be omitted. If protection of graduation markings M from abrasion is not required, the extension of film over those markings may be omitted. If a piston stop is molded integrally with the barrel 11, mass 22 may be omitted. However, the best mode known to the applicant is to employ all of the parts shown in FIGS. 1 and 2.

An embodiment of the frangible film seal applied to a device other than a syringe is shown in FIG. 5, a perspective view of a stopcock after manufacture and before use. A hollow body 31, shown partially cut away in FIG. 5, has a bottom boundary wall 34, a conical side boundary wall 32 and a top boundary wall 33 which define an interior space 46. A hole 37 in top boundary wall allows communication between space 46 and the outside of the body. Flow passageways 35 and 36 also communicate with the interior space and the outside of the body. Caps 38 and 39 are provided for sealing passageways 35 and 36, with associated film extensions 47 and 48. Caps 38 and 39 are releasably mounted to the outside of body 31, and film extensions 47 and 48 adhere to body 31, and caps 38 and 39, respectively. A handle 40 extends through hole 37 from an end 41 within interior space 46 to an end 42 outside of body 31. Plug 43, positioned within interior space 46 in rotatable sealing engagement with side boundary wall 32, has a bore 44 through it and is attached to handle 40 at end 41. Plug 43 provides a means of controlling the flow of a fluid into and out of the interior space. It may be turned by means of handle 40 to a position where bore 44 is aligned with flow passageways 35 and 36, allowing flow into and out of the interior space, or to a position where bore 44 is not aligned and flow is stopped. A continuous, frangible film 45, formed integrally with extensions 47 and 48, extends from top boundary wall 33 of body 31 to handle 40 around the entire perimeter of hole 37 to completely seal the hole during storage. Because film 45 adheres to body 31 and handle 40, it is broken by rotary motion of handle 40. Because extensions 47 and 48 adhere to caps 38 and 39, respectively, they are broken by removal of caps 38 and 39.

Film 45 may be applied by a dipping process modeled on the process set forth for syringes above, or it may be cut from a sheet and sealed to body 31 by conventional heat-sealing techniques, or by other compatible techniques.

Both the syringe depicted in FIGS. 1 through 4 and the stopcock depicted in FIG. 5 may be made from parts which are sterilized before assembly an then assembled under aseptic techniques. However, it is generally more economical to sterilize the entire assembly after all other manufacturing steps have been completed. If this is done, then sterilization is generally performed by means which will penetrate the materials of construction without damaging them. Gamma and beta irradiation are the preferred means.

Thus, the present invention provides a self-packaged medical device which meets the requirements as set forth above and which protects the cleanliness of those devices during storage. A frangible seal affords the protection, the seal being readily broken by movement of one of the movable parts of the device which has been coated with the seal.

What is claimed is:
1. An improved self-packaged medical device for dispensing fluids of the type having:
   (a) a hollow body with boundary walls defining an interior space, a hole in a boundary wall for communication between the interior space and the outside of the body, and a flow passageway through a boundary wall communicating with the interior space and the outside of the body;
   (b) a handle extending through said hole from an end within said interior space to an end outside of the body;
   (c) means for controlling flow of a fluid into and out of the interior space positioned within the interior space and attached to the handle for motion therewith; and
   (d) releasable means for sealing said flow passageway during storage, wherein the improvement comprises: a continuous, frangible film extending from said body to said handle around the entire perimeter of said hole to completely seal said hole against entry of microorganism until the handle is moved, said film adhering to the body and the handle and being readily fractured upon motion of the handle to thereby allow free movement between said handle and said body.

2. A device as defined in claim 1 wherein said film is a flexible material which elongates upon stretching just before fracturing, said elongation leaving a visual indication of said fracture.

3. In a self-packaged medical device for dispensing liquids of the type having a hollow body for receiving said liquid, an operative element within said hollow body adapted to control the flow of liquid out of said body, and means extending from said operative element outwardly through an opening in said body for operating said element and thereby controlling the flow of said liquid, wherein the improvement comprises: a continuous, frangible film extending from said body to said extending means and adhering to the same, and sealing said opening in the space between said body and said extending means to protect said opening from the entry of contaminating media, said film being readily fractured upon operation of said extending means relative to said body whereupon said device may be used to dispense liquid therefrom.

4. A device as defined in claim 3, wherein said device is a hypodermic syringe with said hollow body being a substantially tubular barrel defining an interior bore having an opening at one of its ends, said barrel having a fluid flow passage through its wall at the other end of said interior bore, and wherein said operative element is a piston within said interior bore in slidable engagement with the inside walls of said barrel, and wherein said extending means is a piston rod connected to said piston and extending outwardly through said bore to a position outside of said barrel, whereupon said film seals the bore between said barrel and said piston rod for protective purposes.

5. A device as defined in claim 4, wherein said piston rod has a transverse dimension smaller than the corresponding transverse dimension of said bore to form a clearance between said piston rod and the walls of said bore.

6. A device as defined in claim 5, further comprising a massed portion of said film adhering to said barrel within said bore to obstruct the sliding motion of said piston.

7. A device as defined in claim 4, wherein said film is a flexible material which elongates upon stretching just before fracturing, said elongation leaving a visual indication of said fracture.

8. A device as defined in claims 2 or 7, wherein said film is a polyvinyl chloride plastisol.

9. A device as defined in claim 4, further comprising a marking on the outside of said barrel and an extension of said film adhering to the outside of said barrel and covering said marking to protect it from abrasion, said film being transparent in order to view said marking.

10. An improved self-packaged hypodermic syringe of the type having:
 (a) a hollow, tubular barrel defining an interior bore which is open to the outside at the proximal end of the barrel, said barrel having a distal end wall closing the distal end of the interior bore and a fluid flow passage through said distal end wall;
 (b) a piston within the interior bore in slidable sealing engagement with the inside walls of said barrel;
 (c) a piston rod connected to said piston at one end of the rod, said rod extending outwardly through the opening in said bore to an end outside of the barrel, there being a clearance space between said piston rod and the inside walls of said barrel;
 (d) releasable means for sealing said fluid flow passage,
wherein the improvement comprises: a continuous, frangible film extending from said barrel to said piston rod and adhering to the same, and sealing said bore in said clearance space to protect it from entry of microorganisms, said film being readily fractured upon movement of said piston rod in said barrel whereupon said syringe is ready for use.

11. A syringe as set forth in claim 10, wherein said means for sealing the fluid flow passage comprises a cap releasably mounted to said barrel overlying the opening of said fluid flow passage on the outside surface of said distal end wall, said syringe further including an extension of said film reaching from the outside surface of said barrel to said cap and adhering to said barrel and said cap, said extension being susceptible to fracture upon removal of the cap.

12. A self-packaged stopcock comprising: a hollow body with boundary walls defining an interior space, a hole in said boundary wall for communication between said interior space and the outside of said body, and two flow passages through a boundary wall, one for the inflow, the other for the outflow of fluids; a rotatable plug inside said hollow body having a bore therethrough, said bore adapted to be aligned with and between said two flow passages so that fluid may pass therethrough, said plug rotatable to mis-align said bore and said flow passages whereupon said plug acts to seal said hollow body to prevent the flow of fluids therethrough: a handle connected to said plug and extending through said hole to a position outside of said body, said handle providing the means for rotating said plug; and a continuous, frangible film extending from said body to said handle and adhering to the same, said film extending around the entire perimeter of said hole to seal said hole from the entry of contaminating media until said handle is rotated, said film being readily fractured upon said motion of the handle to thereby allow free movement between said handle and said body.

13. A method of making a self-packaged hypodermic syringe comprising the steps of:
 (a) assembling a piston having a piston rod connected thereto into a bore of a tubular barrel with said piston rod extending out of said barrel, there being a clearance space between said rod and the inside wall of said barrel;
 (b) dipping said assembly so that the end with said extending piston rod faces downward into a bath of curable liquid plastic material which adheres to the piston rod and barrel when cured, said assembly being dipped to a depth sufficient to cause a column of liquid plastic to rise into said clearance space in said barrel;
 (c) withdrawing said assembly from said bath; and
 (d) curing said liquid plastic material to a solid form.

* * * * *